(12) United States Patent
Sliwa et al.

(10) Patent No.: US 9,833,217 B2
(45) Date of Patent: Dec. 5, 2017

(54) METHODS AND APPARATUS FOR UTILIZING IMPELLER-BASED ROTATIONALLY-SCANNING CATHETERS

(75) Inventors: John W. Sliwa, Los Altos Hills, CA (US); Zhenyi Ma, San Jose, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 2547 days.

(21) Appl. No.: 12/347,116

(22) Filed: Dec. 31, 2008

(65) Prior Publication Data

US 2010/0168570 A1  Jul. 1, 2010

(51) Int. Cl.
| | |
|---|---|
| *A61B 8/12* | (2006.01) |
| *A61B 8/00* | (2006.01) |
| *A61B 18/02* | (2006.01) |
| *A61B 18/14* | (2006.01) |
| *A61B 18/18* | (2006.01) |
| *A61B 18/20* | (2006.01) |
| *A61B 18/00* | (2006.01) |
| *A61N 7/02* | (2006.01) |
| *A61B 90/00* | (2016.01) |

(52) U.S. Cl.
CPC ............. *A61B 8/4461* (2013.01); *A61B 8/12* (2013.01); *A61B 8/4281* (2013.01); *A61B 8/445* (2013.01); *A61B 18/02* (2013.01); *A61B 18/14* (2013.01); *A61B 18/18* (2013.01); *A61B 18/20* (2013.01); *A61B 2018/00029* (2013.01); *A61B 2090/3782* (2016.02); *A61B 2090/3784* (2016.02); *A61B 2218/002* (2013.01); *A61N 7/02* (2013.01); *A61N 7/022* (2013.01)

(58) Field of Classification Search
CPC ......... A61B 18/02; A61B 18/14; A61B 18/18; A61B 18/20; A61B 2018/00029; A61B 2090/3782; A61B 2090/3784; A61B 2218/002; A61B 8/12; A61B 8/4281; A61B 8/445; A61B 8/4461; A61N 7/02; A61N 7/022
USPC .................................................. 600/437, 471
See application file for complete search history.

(56) References Cited

U.S. PATENT DOCUMENTS

| | | | | | |
|---|---|---|---|---|---|
| 5,271,402 | A | * | 12/1993 | Yeung | A61B 8/12 600/437 |
| 5,435,314 | A | * | 7/1995 | Dias | 600/463 |
| 5,606,975 | A | * | 3/1997 | Liang | A61B 8/12 600/437 |
| 5,658,515 | A | * | 8/1997 | Lee | B29C 33/42 205/70 |

(Continued)

*Primary Examiner* — Jennifer Dieterle
*Assistant Examiner* — Vani Gupta
(74) *Attorney, Agent, or Firm* — Wiley Rein LLP

(57) ABSTRACT

An ablation catheter includes a tubular catheter body having a lumen, a tip portion, a liquid inlet, at least one liquid outlet, a liquid flow path defined between the liquid inlet and the liquid outlet, and an ablation element mounted on the tip portion of the catheter body. A rotationally-scanning ultrasound assembly is disposed within the lumen of the catheter body adjacent the tip portion. The ultrasound assembly includes an ultrasound transducer having an active face, an acoustic mirror acoustically coupled to the active face of the ultrasound transducer, and an impeller positioned in the liquid flow path and operably coupled to at least one of the ultrasound transducer and the acoustic mirror to impart rotational motion thereto when a liquid flows through the impeller.

31 Claims, 2 Drawing Sheets

(56) References Cited

U.S. PATENT DOCUMENTS

| | | | |
|---|---|---|---|
| 6,004,269 | A | 12/1999 | Crowley et al. |
| 6,004,271 | A | 12/1999 | Moore |
| 6,102,933 | A * | 8/2000 | Lee et al. .................... 606/209 |
| 6,117,101 | A | 9/2000 | Diederich et al. |
| 6,212,426 | B1 | 4/2001 | Swanson |
| 6,277,077 | B1 | 8/2001 | Brisken et al. |
| 6,292,681 | B1 | 9/2001 | Moore |
| 6,383,151 | B1 | 5/2002 | Diederich et al. |
| 6,569,160 | B1 * | 5/2003 | Goldin ................ A61B 18/12 600/427 |
| 6,599,288 | B2 | 7/2003 | Maguire et al. |
| 6,752,805 | B2 | 6/2004 | Maguire et al. |
| 7,494,484 | B2 * | 2/2009 | Beck ............... A61B 17/22012 604/509 |
| 7,852,485 | B2 * | 12/2010 | Alphonse ........... A61B 5/0066 356/479 |
| 7,853,316 | B2 | 12/2010 | Milner |
| 7,935,102 | B2 * | 5/2011 | Breznock ............... A61M 5/36 604/122 |
| 8,187,270 | B2 * | 5/2012 | Auth ................ A61B 18/1492 606/41 |
| 8,989,849 | B2 * | 3/2015 | Milner ............... A61B 5/0066 600/182 |
| 2005/0137478 | A1 | 6/2005 | Younge et al. |
| 2005/0222554 | A1 | 10/2005 | Wallace et al. |
| 2006/0095022 | A1 | 5/2006 | Moll et al. |
| 2006/0100610 | A1 | 5/2006 | Wallace et al. |
| 2007/0167821 | A1 * | 7/2007 | Lee et al. .................... 600/463 |
| 2007/0167826 | A1 * | 7/2007 | Lee et al. .................... 600/463 |
| 2008/0108867 | A1 * | 5/2008 | Zhou ............................ 600/104 |

* cited by examiner

METHODS AND APPARATUS FOR UTILIZING IMPELLER-BASED ROTATIONALLY-SCANNING CATHETERS

BACKGROUND OF THE INVENTION a. Field of the Invention

The instant invention relates to methods and apparatus for scanning a site of interest and providing information about structures within and around the site. In particular, the instant invention relates to rotationally-scanning transducers (e.g., ultrasound transducers, optical transducers such as infrared radiation and optical coherence tomography (OCT) transducers, and the like) that provide visualization of and/or information about adjacent structures.

b. Background Art

Ultrasound transducers are utilized in a variety of medical applications. In many applications, the transducer is mounted in a catheter than can be navigated through a patient's vasculature to a site of interest.

In many such catheters, the transducer is rotated around a longitudinal axis of the catheter in order to perform a B-scan in a plane perpendicular to the axis of the catheter. Such a catheter is referred to herein as a "rotationally-scanning ultrasound catheter." The transducer may be rotated via a motor or a manual actuator (e.g., a finger slider), either of which necessitates a relatively complex, relatively large diameter, and expensive catheter structure. For example, a motorized rotating transducer typically requires a rotating drivewire, a rotating energized ("hot") lead, and a rotating ground lead, as well as electrical slip rings in the catheter handle.

BRIEF SUMMARY OF THE INVENTION

An object of the present invention is to provide a rotationally-scanning catheter having reduced complexity.

Another object of the present invention is to provide a less costly rotationally-scanning catheter.

Still another object of the present invention is to provide a rotationally-scanning catheter having a reduced outer diameter (French size).

Yet another object of the present invention is to provide a rotationally-scanning catheter that permits the introduction of other devices therethrough.

A further object of the present invention is to provide a rotationally-scanning catheter with improved transducer heat-sinking.

An additional object of the present invention is to provide a rotationally-scanning catheter that exhibits reduced acoustic ringing seen in near-field images.

Disclosed herein is a catheter including: a tubular catheter body having a tip portion and a lumen; a rotationally-scanning ultrasound assembly disposed adjacent the tip portion, the rotationally-scanning ultrasound assembly comprising an ultrasound transducer having an active face; and a rotational drive assembly including an impeller operably coupled to the rotationally-scanning ultrasound assembly such that a liquid flowing through the impeller imparts rotational motion to the ultrasound assembly. In some embodiments of the invention, the impeller is operably coupled to the ultrasound transducer to impart rotational motion to the ultrasound transducer. In other embodiments of the invention, the ultrasound assembly further includes an acoustic mirror or reflector adapted to be acoustically coupled to the active face of the ultrasound transducer via an acoustic coupling medium, and the impeller is operably coupled to the acoustic mirror to impart rotational motion to the acoustic mirror while the transducer is non-rotating. The liquid flowed through the impeller may also be the acoustic coupling medium. Typically, the ultrasound assembly is oriented to provide a visualization field adjacent the tip portion of the catheter body.

Where an acoustic mirror is utilized, the acoustic mirror may be positioned proximally of the ultrasound transducer (with the active face of the ultrasound transducer facing proximally) or distally of the ultrasound transducer (with the active face of the ultrasound transducer facing distally). Alternatively or in addition to an acoustic mirror, the ultrasound assembly may include an acoustic lens adapted to be acoustically coupled to the active face of the ultrasound transducer via an acoustic coupling medium. In some embodiments, an acoustic focusing effect may be provided by shaping an acoustic mirror or reflector to be other than flat.

The impeller may include a central passageway to accommodate at least one non-rotating electrical wire routed through the lumen. This central passageway may also serve as a recycling pathway for a liquid after it passes through the impeller. It is desirable, however, for at least some liquid to be exhausted in vivo adjacent the tip portion. To this end, the lumen of the catheter body may also include a plurality of outlet ports to exhaust a liquid flowing through the impeller in vivo (e.g., adjacent the tip portion).

It is desirable for the impeller to rotate at between about 10 rpm and 20 rpm. To this end, two or more of an impeller blade rake angle, a liquid flow rate, and a liquid pressure may be selected and/or controlled. This rate of rotation provides suitable image frame rates with a minimum refresh rate. Of course, faster rotation rates may be utilized to obtain higher image frame rates without departing from the spirit and scope of the present invention.

Optionally, the tip portion of the catheter body includes an ablation element, such as an RF ablation element. Alternatively, the ultrasound transducer itself may serve as an ablation element. Optionally, the ultrasound transducer may be employed to sonically remove plaque in lumens, such as blood vessels.

In another embodiment of the invention, an ablation catheter includes a tubular catheter body including: a lumen; a tip portion; a liquid inlet; at least one liquid outlet; and a liquid flow path defined between the liquid inlet and the liquid outlet. An ablation element may be mounted on the tip portion of the catheter body, and a rotationally-scanning ultrasound assembly may be disposed within the lumen of the catheter body adjacent the tip portion. The rotationally-scanning ultrasound assembly includes: an ultrasound transducer having an active face; an acoustic mirror acoustically coupled to the active face of the ultrasound transducer; and an impeller positioned in the liquid flow path and operably coupled to at least one of the ultrasound transducer and the acoustic mirror to impart rotational motion thereto when a liquid flows through the impeller. A fluid, such as saline, may be disposed between the ultrasound transducer and the acoustic mirror to acoustically couple the acoustic mirror to the active face of the ultrasound transducer. The impeller may be rotationally driven in one or both directions, depending upon the direction of flow into/through the impeller.

In some embodiments of the invention, the acoustic mirror and the impeller are formed as a unitary assembly. In other embodiments of the invention, the acoustic mirror is affixed to the impeller.

To provide a desirable visualization field adjacent the tip portion of the catheter body, at least one of the ultrasound transducer and the acoustic mirror may be oriented non-orthogonally to a central axis of the catheter body. Typically, the image plane will be a 90 degree oriented circular disk, though it is within the ambit of the present invention to scan a cone-shaped surface at an angle other than 90 degrees to the longitudinal axis of the tubular catheter body.

It is also desirable for the tubular catheter body to be formed of a material selected to minimize reflections and ringing of ultrasonic energy propagating therethrough. Typically, this material will have an acoustic impedance near that of water or tissue and will have a low, water-like attenuation. One suitable material for such an "acoustic window" is polyethylene.

In some embodiments of the invention, the at least one liquid outlet is positioned to exhaust a liquid flowing through the liquid flow path adjacent the tip portion. Alternatively, the liquid flow path may include an outlet segment between the impeller and the at least one liquid outlet configured to return a liquid flowing through the liquid flow path to a proximal end of the catheter. Of course, a combination of the two arrangements (e.g., partial exhaustion and partial recycling) is also contemplated.

According to another aspect of the invention, a method of assessing tissue includes the following steps: providing a catheter including a tubular catheter body having a tip portion, an ablation element mounted on the tip portion, and a lumen, a rotationally-scanning ultrasound assembly disposed within the lumen adjacent the tip portion and including an ultrasound transducer having an active face, wherein the ultrasound assembly provides a visualization field adjacent the tip portion of the catheter body, and an impeller operably coupled to the ultrasound assembly to impart rotational motion thereto; placing the tip portion of the catheter adjacent tissue to be assessed; and flowing a liquid through the impeller, thereby rotating the ultrasound assembly. The liquid may be exhausted adjacent the tip portion to irrigate the tissue to be assessed, recycled, or a combination of both. The method may also include monitoring a rotational position of the ultrasound assembly. In addition, the method may optionally include generating a three dimensional image of and/or monitoring creation of an ablation lesion within a tissue within the visualization field.

In still another aspect of the invention, a method of manufacturing an ablation catheter includes the following steps: providing a tubular catheter body having a tip portion and a lumen; mounting an ablation element on the tip portion; placing a rotationally-scanning ultrasound assembly within the lumen adjacent the tip portion, the ultrasound assembly including a transducer; and operably coupling an impeller to the ultrasound assembly to impart rotational motion to the ultrasound assembly when a liquid flows through the impeller. The impeller may be micromolded and operably coupled to the transducer, to an acoustic mirror acoustically coupled to the transducer, or to both the transducer and an acoustic mirror acoustically coupled to the transducer. Of course, the impeller may be micromolded as a unitary assembly with the acoustic mirror and/or a backing for the acoustic mirror. The term "micromolded" includes polymer molding, powder metallurgy, metal particle sintering, and the like.

In some embodiments, the impeller includes a central passageway, and the method includes the additional steps of: providing at least one non-rotating lead; attaching an end of the at least one lead to at least one of the ablation element and the transducer; and routing the lead proximally through the central passageway of the impeller. Non-rotating leads routed through the impeller may also be contained in a non-rotating microtube that may also act as an electrode and/or as a rotational bearing surface in some embodiments of the invention.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides a rotationally-scanning (e.g., including an ultrasound and/or optical imaging or non-imaging transducer) catheter suitable for use in the human vasculature or under blood for medical procedures, such as cardiac diagnostic and therapeutic procedures including, without limitation, tissue assessment and cardiac ablation. Though the present invention will be described in connection with a rotationally-scanning ultrasound cardiac catheter, it is contemplated that the described features may be incorporated into any number of catheters or other devices adapted to navigate and "inspect" structures within and around a narrow vessel or other structure, as would be appreciated by one of ordinary skill in the art. While the depicted embodiments will be described primarily with reference to and in the context of one or more ultrasound transducers disposed within a catheter, other types of transducers and/or supporting structures therefor are intended as within the scope of the invention.

Figure 1:
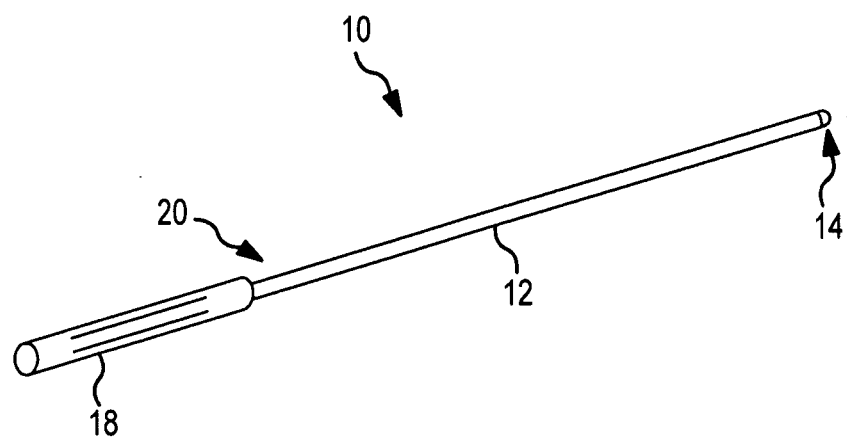
FIG. 1 illustrates a catheter according to the present invention.

FIG. 1 depicts a catheter 10 according to a first embodiment of the present invention. Catheter 10 generally includes a tubular catheter body or shaft 12 having a tip portion 14 and defining a lumen 16 (visible in FIG. 2). In some forms, catheter body 12 may define more than one lumen 16. A handle 18 may be coupled to a proximal end 20 of catheter body 12. In addition, catheter 10 may include electrical connections and/or fluid supply connections (not shown) as discussed in greater detail below. Such connections may conveniently be provided as part of handle 18.

Figure 2:
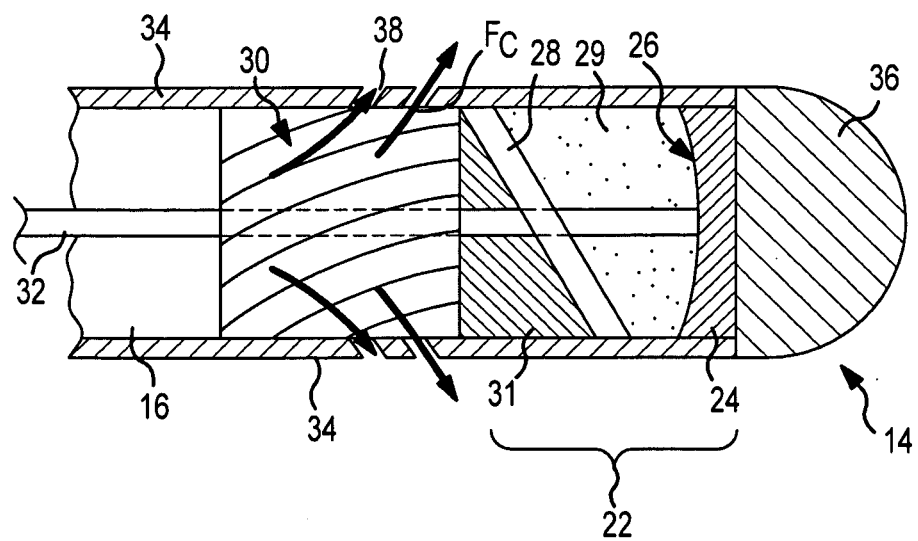
FIG. 2 is a detailed view of the tip region of the catheter of FIG. 1.

FIG. 2 is a cutaway detail of tip portion 14 and the adjacent region of catheter body 12. A rotationally-scanning ultrasound assembly 22 is disposed within lumen 16 adjacent tip portion 14. Ultrasound assembly 22 includes an ultrasound transducer 24 having an active face 26. Ultrasound transducer 24 may be a phased array transducer, a mechanically focused transducer, a lens focused transducer, an imaging transducer, or any other type of ultrasound transducer. Of course, it is within the spirit and scope of the present invention to utilize non-ultrasound transducers, such as optical coherence imaging optics, as well. One of ordinary skill in the art will appreciate how to select a suitable transducer for a particular application of catheter 10. In the example of FIG. 2, transducer 24 is depicted as a spherically-focused, single-element piezoetransducer. Though the invention will be described primarily in connection with a non-rotating ultrasound transducer 24, it should be understood that ultrasound transducer 24 may rotate without departing from the spirit and scope of the present invention. Thus, as described in further detail below, transducer 24 may or may not rotate in a given embodiment of catheter 10. As also explained below, the use of a non-rotating transducer 24 advantageously eliminates the need for rotating wires and electrical contact sliprings.

In some embodiments of the invention, ultrasound assembly 22 further includes an acoustic mirror 28 adapted to be acoustically coupled to active face 26 of transducer 24. Acoustic mirror 28 may be acoustically coupled to transducer 24 via an acoustic coupling medium 29, such as liquid saline, disposed within lumen 16 between acoustic mirror 28 and transducer 24. Alternatively, acoustic mirror 28 may become acoustically coupled to transducer 24 when an acoustic coupling medium, such as saline, is flowed through lumen 16. The use of a liquid acoustic coupling medium between transducer 24 and acoustic mirror 28 advantageously acts as an acoustic delay line, thereby improving near-field imaging assessments by assuring that immediate ringdown artifacts can be effectively gated out in a known manner. The use of a liquid acoustic coupling medium also advantageously acts as a heat sink for transducer 24, allowing for higher power and longer duration operation thereof, particularly when the couplant is a flowed liquid such as saline.

Those of skill in acoustic design will appreciate that it is desirable for an acoustic mirror to have a high acoustic impedance mismatch with the acoustic coupling medium (e.g., saline). Thus, materials that are air-like (e.g., air-filled foam) and heavy metals (e.g., tungsten and stainless steel) make suitable acoustic mirrors.

A number of configurations of ultrasound assembly 22 are contemplated. For example, in some embodiments of the invention, acoustic mirror 28 is positioned proximally of transducer 24. In these embodiments, active face 26 of transducer 24 faces proximally. In alternative embodiments of the invention, acoustic mirror 28 may be positioned distally of transducer 24 and active face 26 of transducer 24 may face distally.

A rotational drive assembly including an impeller 30 or turbine (e.g., an impeller with a housing) is operably coupled to rotationally-scanning ultrasound assembly 22 in order to impart rotational motion thereto. When a liquid or other fluid, such as saline or a gas, flows through or past impeller 30, it causes impeller 30 to rotate. Rotation of impeller 30, in turn, causes rotationally-scanning ultrasound assembly 22 (e.g., transducer 24 and/or acoustic mirror 28) to rotate. The use of a liquid medium to rotate impeller 30 is desirable, as it can be exhausted in vivo and will provide more torque and faster rotational acceleration and deceleration.

In some embodiments of the invention, impeller 30 is operably coupled to acoustic mirror 28 such that acoustic mirror 28 rotates while transducer 24 remains stationary. In other embodiments of the invention, impeller 30 is operably coupled to transducer 24 such that transducer 24 rotates while acoustic mirror 28 remains stationary. Of course, it is contemplated that impeller 30 may be operably coupled to both acoustic mirror 28 and transducer 24 such that both acoustic mirror 28 and transducer 24 rotate.

As discussed in further detail below, the invention advantageously enables the avoidance of the need for costly and space-hogging rotational drive shafts, rotating electrical wires or leads, electrical sliprings, and the like, while still allowing rotational scanning. For example, in embodiments of the invention where transducer 24 is stationary (e.g., non-rotating), it could have its "hot" and "ground" leads routed through one or more of lumen 16 (e.g., adjacent wall 34), through central passageway 32 (as discussed in further detail below), or through wall 34 of catheter body 12. One of skill in the art will appreciate that these electrodes need not rotate if transducer 24 is static (e.g., if impeller 30 is operably coupled only to acoustic mirror 28). Of course, it is contemplated that prior art rotating transducer assemblies can be employed in conjunction with the teachings of the present invention.

By appropriately selecting and controlling impeller blade rake angle, liquid flow rate through the impeller, and liquid pressure into the impeller, the speed at which impeller 30 rotates can be controlled. In some embodiments of the invention, at least two of these three variables are selected and/or controlled such that impeller 30 rotates at between about 10 rpm and about 20 rpm. It should also be understood that the liquid that causes impeller 30 to rotate may also serve to acoustically couple transducer 24 and acoustic mirror 28 as described above. The liquid also advantageously allows for cooling of transducer 24 and to flush any blood, debris, tissue, and/or bubbles away. In addition, the liquid may also act to irrigate tip portion 14 if tip portion 14 includes an ablation element (described below)

Impeller 30 may be formed via micromolding (e.g., polymer micromolding), which advantageously reduces the cost of manufacturing impeller 30. In some embodiments of the invention, impeller 30 and acoustic mirror 28 are formed as a unitary assembly, for example by micromolding. In other embodiments of the invention, impeller 30 and acoustic mirror 28 are separately formed and are affixed to one another, such as by adhesive or ultraviolet bonding or the like, during manufacture of catheter 10. For example, impeller 30 and acoustic mirror 28 may each be mounted to a mirror backing 31. In some embodiments, acoustic mirror 28 and mirror backing 31 may be formed as a unitary subassembly (e.g., of stainless steel) that is affixed to impeller 30. Alternatively, acoustic mirror 28, mirror backing 31, and impeller 30 may all be formed as a unitary assembly (e.g., of an acoustically-reflective material), for example by molding, micromolding, powder metallurgy, laser-sintering, machining, laser micromachining, or the like.

One or more of impeller 30, acoustic mirror 28, and transducer 24 may include a central passageway or conduit 32. Central passageway 32 accommodates one or more non-rotating electrically conductive insulated leads (not shown), such as transducer hot leads, transducer ground leads, RF hot leads, thermocouple leads, thermistor leads, or the like. These leads may be independent or shared, and will typically be electrically coupled at one end to transducer 24, an ablation element (described below), or another electric component of catheter 10 (e.g., a temperature sensor such as a thermistor or thermocouple, a pressure sensor, etc.). The lead(s) may then be routed proximally through central passageway 32 to be connected to a suitable connector (not shown), which may be incorporated in or attached to handle 18. The lead(s) may also be encased in a tube, such as a hypodermic microtube, that is inserted within central passageway 32. This latter arrangement is desirable where central passageway 32 is also used to pass liquids, for example to recycle saline used to drive impeller 30. Fiber optics could also be passed through central passageway 32.

Though central passageway 32 is coaxial with the axis about which ultrasound assembly 22 rotates, it does not necessarily act as a bearing for the rotating component or components of ultrasound assembly 22. Instead, as can be the case with polymeric deformable impellers, the blades of impeller 30 may serve as flexible bearing surfaces against the wall 34 of catheter body 12.

Tip portion 14 of catheter body 12 may also include an ablation element 36 as shown in FIG. 1. In certain embodiments of the invention, ablation element 36 includes at least one RF ablation element, though ablation element 36 could also include a laser ablation element, a thermal ablation element, a high intensity focused ultrasound (HIFU) ablation element, a microwave ablation element, a chemical ablation element, a cryogenic ablation element, or any other type of ablation element. One of ordinary skill in the art will appreciate how to select a suitable ablation element or elements for a particular application of catheter 10. Moreover, where HIFU ablation is desired, transducer 24 may serve as a HIFU ablation element. Alternatively, or in addition, tip portion 14 of catheter body 12 may carry a pacing or sensing electrode instead of or in addition to ablation element 36. Electrodes on catheter body 12 (e.g., on tip portion 14) may also be employed to aid in navigation of catheter 10 through the patient's vasculature.

It should also be recognized that the electrode or electrodes could be provided at the tip of catheter 10 and/or around the circumferential surface of the tip. A very thin metallic circumferential electrode beneficially should not interfere significantly within incoming/outgoing acoustics passing through it (e.g., it should be substantially acoustically transparent).

In an embodiment, ultrasound assembly 22 is oriented to provide an ultrasound visualization field laterally adjacent tip portion 14 of catheter body 12. Thus, the visualization field may form an angle with the longitudinal axis of catheter 10 of up to about 90 degrees, and preferably between about 45 degrees and about 90 degrees. This orientation allows ultrasound assembly 22 to be used for imaging adjacent tip portion 14 (e.g., tissue elasticity imaging, Doppler flow imaging, volumetric imaging, etc.) as well as for assessment of adjacent tissue (e.g., pre-inspection of a potential lesion site, ablation lesion feedback, post-ablation inspection of a lesion site, determining the location of anatomical structures, detecting tissue-popping or potential popping due to steam bubbles, thickness information regarding adjacent tissue or fat deposits, etc.). Thus, both imaging and non-imaging modalities are supported according to certain embodiments, but the "visualization field" (or "field of view") of the transducer may be provided during design by orienting at least one of acoustic mirror 28 and transducer 24 non-orthogonally to a central axis of catheter body 12. Although some embodiments of the invention will employ continuous rotation of ultrasound assembly 22, it is contemplated that stepped rotation may be employed in other embodiments of the invention.

The term "adjacent tissue" refers to tissue that is in contact or nearly in contact with catheter body 12, as well as tissue that is within the field of view of transducer 24. Thus, catheter 10 may be utilized where there is actual or near contact, such as for lumen wall inspection or inspection of a nearby or contacting cardiac chamber wall, as well as to collect multiple image planes, such as may be desirable to construct a three dimensional image or model. In the latter application, tip portion 14 may be suspended in the middle of a cardiac blood pool and translated along its axial length in order to access the multiple image planes.

It is also desirable to form catheter body 12 out of a material selected to minimize reflections and ringing of ultrasonic (and other suitable transducer) energy propagating therethrough (for example, a low-loss acoustic propagation path or an optically transparent material in the case of an optical transducer). One suitable material for catheter body 12 is polyethylene. Alternatively, catheter body 12 may have an open-cage type construction such that its structural members can be substantially ignored in the acoustic data. It is also contemplated that only that portion of catheter body 12 through which ultrasound energy passes (e.g., that portion of catheter body 12 within the beampath of transducer 24) may be substantially acoustically transparent—that is, it is contemplated that catheter body 12 may include an acoustic window or hole portion where ultrasound energy is to be passed.

A liquid or other fluid (e.g., saline) used to turn impeller 30 will typically be introduced into lumen 16 via a liquid inlet (or, alternatively, multiple liquid inlets) positioned at proximal end 20 of catheter body 12. For example, a manifold (not shown) may be provided as part of or connected to handle 18. The manifold may be connected to a reservoir of a liquid, such as saline. The liquid may be provided by a positive displacement pump or a pressure-settable bag. Of course, the liquid inlet(s) may be positioned elsewhere on catheter body 12 without departing from the spirit and scope of the present invention. A liquid flow path, which passes through impeller 30, is defined between the liquid inlet(s) and at least one liquid outlet. Several liquid outlet configurations are contemplated.

Figure 3:
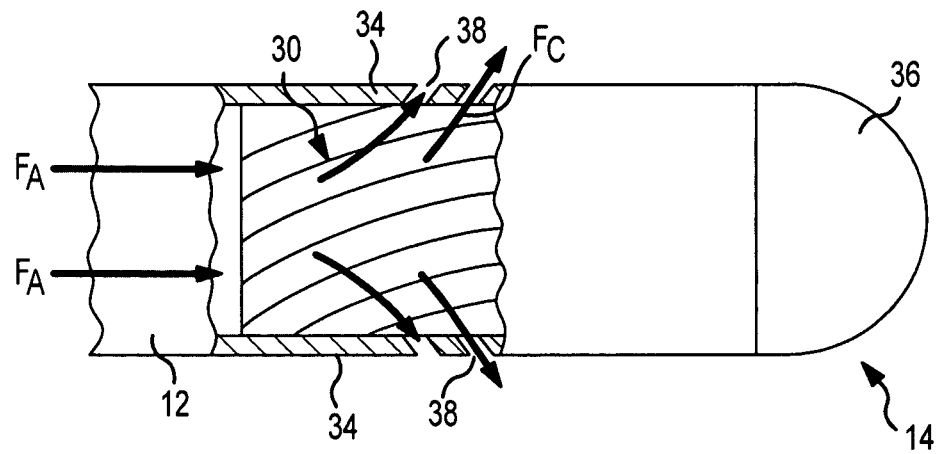
FIG. 3 is a partial cut-away detailed view of the tip region of the catheter of FIG. 1 illustrating liquid outlets configured to irrigate adjacent tissue.

FIG. 3 is a partial cutaway detail of one embodiment of tip portion 14 and the adjacent region of catheter body 12 depicting a plurality of liquid outlets 38 in wall 34 that permit the liquid driving impeller 30 to be exhausted in vivo. Liquid outlets 38 allow a liquid to be introduced into lumen 16 (arrows $F_A$), flowed through impeller 30 to rotate ultrasound assembly 22 (e.g., transducer 24 and/or acoustic mirror 28), and then exit lumen 16 through liquid outlets 38 adjacent tip portion 14 (arrows $F_C$). The liquid may beneficially be used as an irrigation fluid to cool adjacent tissue, to acoustically couple ultrasound assembly 22 to adjacent tissue, and/or to convey ablating energy from ablation element 36 to tissue being lesioned. The exhausted liquid may also act to provide the advantages related with a saline-irrigated RF catheter.

Rather than being entirely exhausted in vivo adjacent tip portion 14, the liquid flow path may alternatively return all or some of the liquid to proximal end 20 of catheter body 12 after passing through impeller 30. This allows all or some of the liquid driving impeller 30 to be recycled, which in turn facilitates higher flow rates and pressures. In addition, a "closed" (or partially closed) flow path allows the liquid driving impeller 30 to be driven in reverse such that the direction in which impeller 30 rotates can be reversed, which may be desirable in some implementations of catheter 10. Thus, one might alternate flow forward and backward, thereby angularly oscillating ultrasound assembly 22 within a controlled angular sector.

Figure 4:
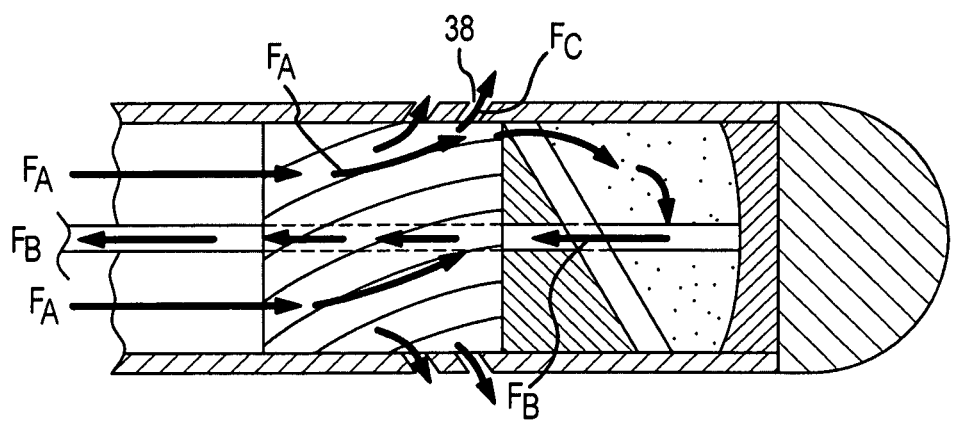
FIG. 4 illustrates a liquid flow path that allows a liquid to be recycled after driving the impeller.

FIG. 4 illustrates an embodiment of catheter 10 that includes an outlet segment between impeller 30 and a liquid outlet (not shown). Arrows $F_A$ depict the incoming flow of liquid (e.g., saline) that turns impeller 30. Once the liquid passes through impeller 30, a portion may be exhausted in vivo through liquid outlets 38 (arrows $F_C$), while a portion of the liquid enters central passageway 32 and returns to the proximal end of catheter 10 as shown by arrows $F_B$. One of ordinary skill in the art will appreciate that the direction in which impeller 30 rotates can be reversed by reversing the direction in which the saline flows.

Of course, it is also within the spirit and scope of the invention for all of the flow to be recycled. It is also contemplated that liquid outlets 38 may be positioned elsewhere along catheter body 12 such that, while a portion of the flow is exhausted in vivo, it is not exhausted adjacent tip portion 14, but rather elsewhere along the length of catheter body 12.

In use, catheter 10 may be introduced into a patient's vasculature and navigated therethrough to a desired location, such as into the patient's heart, until tip portion 14 is placed adjacent tissue (e.g., in contact with the tissue, in near contact with the tissue, or such that the tissue is within the visualization field) to be assessed and/or ablated. A liquid, such as saline, may then be forcibly flowed through impeller 30, thereby rotating ultrasound assembly 22 (e.g., transducer 24 and/or acoustic mirror 28). One of ordinary skill in the art will appreciate that impeller 30, and therefore ultrasound assembly 22, may be rotated continuously or in steps through any degree of rotation (e.g., partial rotation, 360 degree rotation, more than 360 degree rotation, etc.). It is also contemplated that impeller 30 may be oscillated (e.g., rotated back and forth) or even rotated in reverse. This, in turn, permits an acoustic beam emitted by transducer 24 to be rotated unidirectionally, bidirectionally, continuously, through one or more rotations or partial rotations or oscillations, and the like. It should be understood that some of these modes of impeller rotation entail backwards and/or pulsed flow through impeller 30. Thus, one might pressure-manipulate the input and/or exhaust sides of the flow path. Alternatively, or in addition, one might control the volume flow rate.

As described above, after flowing through impeller 30, the liquid may either be exhausted adjacent tip portion 14, for example in order to irrigate the tissue being assessed or, alternatively, returned to proximal end 20 of catheter body 12 to be recycled.

It is also contemplated that the rotation position of ultrasound assembly 22 and/or impeller 30 may be monitored. This can be accomplished, for example, by monitoring a volume of liquid passing through impeller 30, by use of an optical encoder, by use of an electromagnetic encoder, by use of data from transducer 24 (e.g., imaging or pinging pulse-echo), by controlling the pressure at which liquid is delivered to impeller 30, by controlling the pressure delta across impeller 30, and any combination thereof. In some embodiments of the invention, catheter body 12 is marked with encoding features that may be detected by transducer 24 while ultrasound assembly 22 rotates. Of course, the pressure and/or rate at which liquid is delivered to impeller 30 may be controlled to achieve a desired rotational position or rotational speed of ultrasound assembly 22.

Advantageously, the use of impeller 30 to rotate ultrasound assembly 22, rather than a more traditional mechanical or electromechanical (e.g., motorized) assembly, allows lumen 16 to remain available for the introduction of other medical devices, even if lumen 16 is also used as a fluid pathway. It also reduces the expense and complexity associated with the manufacture of a rotationally-scanning ultrasound catheter, which in turn permits the manufacture of smaller French size rotationally-scanning ultrasound catheters.

Although several embodiments of this invention have been described above with a certain degree of particularity, those skilled in the art could make numerous alterations to the disclosed embodiments without departing from the spirit or scope of this invention.

For example, though rotationally-scanning ultrasound assembly 22 has been described as positioned adjacent tip portion 14, it is contemplated that ultrasound assembly 22 may equally well be positioned within tip portion 14.

Further, ultrasound assembly 22 may be configured to slide along the length of catheter body 12, which would facilitate three dimensional imaging without substantial movement of catheter body 12. Of course, three dimensional imaging may also be collected by moving the catheter such that the image plane is scanned through a volume. Exemplary three dimensional images are of a lumen wall or a cardiac chamber or valve, and may be overlaid upon and/or registered to another type of diagnostic image (e.g., an electrophysiology map or model), for example to monitor or control an ablation; one or more microprocessors running on one or more computers may be employed to collect, interpret, and output these three dimensional images.

As another example, ultrasound assembly 22 could include an acoustic lens acoustically coupled to active face 26 of transducer 24 instead of or in addition to acoustic mirror 28.

As yet another example, multiple impellers 30 could be provided to impart rotational motion to ultrasound assembly 22. These impellers may be arranged to rotate in the same direction or to counter-rotate with respect to each other.

Moreover, it should be understood that transducer 24 may both emit energy (e.g., ultrasound energy) and receive energy (e.g., ultrasound energy). Of course, an acoustic lens, acoustic mirror, or acoustic reflector may be mechanically focused, such as by shaping.

Further, rather than using the fluid that drives impeller 30 to irrigate, separate pathways through lumen 16 could be provided for irrigation, heat sinking, and the like.

In addition, though the invention has been described as including a saline-driven impeller or turbine, the invention could be practiced to good advantage with any structure that rotates when any flowable medium (saline or otherwise) is forced past or through it. For example, in the case of a cryogenic ablation element, the flowed fluid may be a cryogen in either liquid or gaseous form.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A catheter comprising:
    a tubular catheter body, configured for insertion into a body, the tubular body having a tip portion and a lumen;
    a rotationally-scanning ultrasound assembly disposed adjacent the tip portion, the rotationally-scanning ultrasound assembly comprising an ultrasound transducer having an active face; and
    a drive assembly including an impeller operably coupled to the rotationally-scanning ultrasound assembly such that a liquid flowing through the impeller imparts rotational motion to the ultrasound assembly, wherein the lumen of the catheter body includes a plurality of outlet ports extending through a wall of the catheter body adjacent the tip portion, wherein the liquid flowing through the impeller, is configured to be exhausted in vivo through the plurality of outlet ports.

2. The catheter according to claim 1, wherein the impeller is operably coupled to the ultrasound transducer to impart rotational motion to the ultrasound transducer.

3. The catheter according to claim 1, wherein the ultrasound assembly further comprises an acoustic mirror adapted to be acoustically coupled to the active face of the ultrasound transducer via an acoustic coupling medium.

4. The catheter according to claim 3, wherein the acoustic coupling medium comprises the liquid flowed through the impeller.

5. The catheter according to claim 3, wherein the impeller is operably coupled to the acoustic mirror to impart rotational motion to the acoustic mirror.

6. The catheter according to claim 5, wherein the ultrasound transducer is non-rotating.

7. The catheter according to claim 3, wherein the acoustic mirror is positioned proximally of the ultrasound transducer.

8. The catheter according to claim 3, wherein the acoustic mirror is positioned distally of the ultrasound transducer.

9. The catheter according to claim 1, wherein the ultrasound assembly further comprises an acoustic lens adapted to be acoustically coupled to the active face of the ultrasound transducer via an acoustic coupling medium.

10. The catheter according to claim 1, wherein the impeller includes a central passageway to accommodate at least one electrical wire routed through the lumen.

11. The catheter according to claim 1, wherein two or more of an impeller blade rake angle, a liquid flow rate, and a liquid pressure are selected or controlled such that the impeller rotates at between about 10 rpm and 20 rpm when the liquid flows into the impeller.

12. The catheter according to claim 1, wherein the tip portion of the catheter body includes an ablation element.

13. The catheter according to claim 12, wherein the ablation element is an RF ablation element.

14. The catheter according to claim 1, wherein the ultrasound assembly is oriented to provide a visualization field adjacent the tip portion of the catheter body.

15. The catheter according to claim 1, wherein the ultrasound assembly is slidably mounted within the lumen of the tubular catheter body.

16. An ablation catheter comprising:
a tubular catheter body, configured for insertion into a body, the tubular body comprising:
a lumen;
a tip portion;
a liquid inlet;
at least one liquid outlet extending through a wall of the catheter body; and a liquid flow path defined between the liquid inlet and the liquid outlet; an ablation element mounted on the tip portion of the catheter body; and
a rotationally-scanning ultrasound assembly disposed within the lumen of the catheter body adjacent the tip portion, the rotationally-scanning ultrasound assembly comprising:
an ultrasound transducer having an active face;
an acoustic mirror acoustically coupled to the active face of the ultrasound transducer; and
an impeller positioned in the liquid flow path and operably coupled to at least one of the ultrasound transducer and the acoustic mirror wherein the impeller is configured to impart rotational motion thereto when a liquid flows through the impeller and wherein the liquid is configured to be exhausted in vivo through the at least one liquid outlet.

17. The catheter according to claim 16, wherein at least one of the ultrasound transducer and the acoustic mirror is oriented non-orthogonally to a central axis of the catheter body such that the ultrasound assembly provides a visualization field adjacent the tip portion of the catheter body.

18. The catheter according to claim 16, wherein the ultrasound transducer is positioned distally of the acoustic mirror and oriented with the active face facing proximally.

19. The catheter according to claim 16, wherein the ultrasound transducer is positioned proximally of the acoustic mirror and oriented with the active face facing distally.

20. The catheter according to claim 16, further comprising a fluid disposed between the ultrasound transducer and the acoustic mirror to acoustically couple the acoustic mirror to the active face of the ultrasound transducer.

21. The catheter according to claim 16, wherein the tubular catheter body comprises a material selected to minimize reflections and ringing of ultrasonic energy propagating therethrough.

22. The catheter according to claim 21, wherein the tubular catheter body comprises polyethylene.

23. The catheter according to claim 16, wherein the acoustic mirror and the impeller are formed as a unitary assembly.

24. The catheter according to claim 16, wherein the acoustic mirror is affixed to the impeller.

25. The catheter according to claim 16, wherein the at least one liquid outlet is positioned to exhaust the liquid flowing through the liquid flow path adjacent the tip portion.

26. The catheter according to claim 16, wherein the liquid flow path includes an outlet segment between the impeller and the at least one liquid outlet, and wherein the outlet segment is configured to return the liquid flowing through the liquid flow path to a proximal end of the catheter.

27. A method of assessing tissue, comprising:
providing a catheter comprising:
a tubular catheter body having a tip portion, an ablation element mounted on the tip portion, and a lumen;
a rotationally-scanning ultrasound assembly disposed within the lumen adjacent the tip portion and including an ultrasound transducer having an active face, wherein the ultrasound assembly provides a visualization field adjacent the tip portion of the catheter body; and
an impeller operably coupled to the ultrasound assembly to impart rotational motion thereto;
placing the tip portion of the catheter adjacent tissue to be assessed;
flowing a liquid through the impeller, thereby rotating the ultrasound assembly; and
exhausting the liquid from the tubular catheter body adjacent the tip portion to irrigate the tissue to be assessed.

28. The method according to claim 27, wherein the ultrasound assembly further comprises an acoustic mirror acoustically coupled to the active face of the ultrasound transducer and operably coupled to the impeller, and wherein the step of flowing a liquid through the impeller comprises flowing the liquid through the impeller to rotate the mirror.

29. The method according to claim 27, further comprising monitoring a rotational position of the ultrasound assembly.

30. The method according to claim 27, further comprising generating a three dimensional image of a tissue within the visualization field.

31. The method according to claim 27, further comprising monitoring creation of an ablation lesion of a tissue within the visualization field.

* * * * *